United States Patent [19]

Wade et al.

[11] 3,969,343

[45] July 13, 1976

[54] TRIAZOLO[4,3-d][1,4]BENZODIAZEPINE-3,6-DIONES

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Jan. 27, 1975

[21] Appl. No.: 544,470

[52] U.S. Cl. .................... 260/239.3 T; 424/269; 260/239.3 D
[51] Int. Cl.² .................................. C07D 487/04
[58] Field of Search ......................... 260/239.3 T

[56] References Cited
UNITED STATES PATENTS

| | | | |
|---|---|---|---|
| 3,894,011 | 7/1975 | Vogt et al. | 260/239.3 T |
| 3,895,005 | 7/1975 | Vogt et al. | 260/239.3 T |

*Primary Examiner*—Henry R. Jiles
*Assistant Examiner*—Robert T. Bond
*Attorney, Agent, or Firm*—Lawrence S. Levinson; Merle J. Smith; Donald J. Barrack

[57] ABSTRACT

Triazolo[4,3-d][1,4]benzodiazepine-3,6-diones having in the 2-position an alkyl, phenyl or arylalkyl substituent are useful anti-inflammatory agents.

16 Claims, No Drawings

TRIAZOLO[4,3-D][1,4]BENZODIAZEPINE-3,6-DIONES

SUMMARY OF THE INVENTION

Compounds having the structure

I 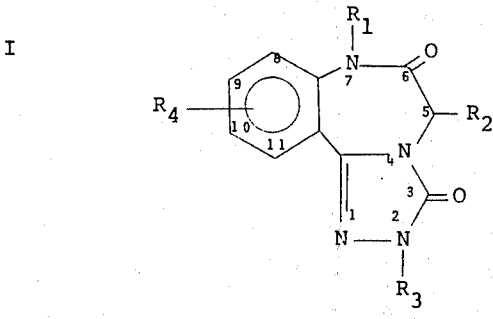

II 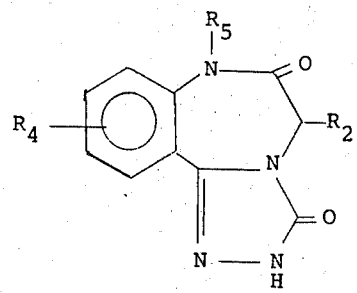

are anti-inflammatory agents.

In formula I, and throughout the specification, the symbols are as defined below:

$R_1$ can be hydrogen, alkyl, phenyl or benzyl;
$R_2$ can be hydrogen or alkyl;
$R_3$ can be alkyl, phenyl or arylalkyl; and
$R_4$ can be hydrogen, halogen (preferably chlorine, fluorine or bromine), nitro, cyano, trifluoromethyl, alkyl, alkoxy or alkylthio.

The term "alkyl", as used throughout the specification, either by itself or as part of a larger group, refers to both straight and branched chain alkyl groups containing 1, 2, 3, or 4 carbon atoms.

The term "alkoxy", as used throughout the specification, refers to a group of the formula Y—O—, wherein Y is alkyl as defined above.

The term "halogen", as used throughout the specification, refers to fluorine, chlorine, bromine, and iodine.

The term "aryl" refers to phenyl or phenyl substituted with 1 or 2 alkyl, alkoxy or halogen substituents. Phenyl and monosubstituted phenyl are preferred aryl groups and phenyl is the most preferred.

The term "arylalkyl", as used throughout the specification, refers to an alkyl group (as defined above) substituted with an aryl group (as defined above). The preferred arylalkyl groups are arylmethyl and arylethyl.

DETAILED DESCRIPTION OF THE INVENTION

The triazolobenzodiazepines of formula I are useful in the treatment of inflammatory conditions in mammalian species, e.g. rats, dogs, cats, monkeys, etc. The compounds can be used to provide relief for joint tenderness and stiffness in conditions such as rheumatoid arthritis.

The compounds of this invention are formulated for use as anti-inflammatory agents according to accepted pharmaceutical practice in oral dosage forms such as tablets, capsules, elixirs or powders, or in an injectable form in a sterile aqueous vehicle prepared according to conventional pharmaceutical practice. The compounds of this invention may be administered in amounts of 100mg/70kg/day to 2g/70kg/day, preferably 100mg/70kg/day to 1g/70kg/day.

The novel compounds of this invention are prepared from triazolo[4,3-d] [1,4]benzodiazepine-3,6-diones having the structure.

In formula II, and throughout the specification, the symbol $R_5$ can be alkyl, phenyl or benzyl.

A triazolobenzodiazepine of formula II can be reacted with an appropriate base, e.g. thallous ethoxide, to obtain a salt having the structure III 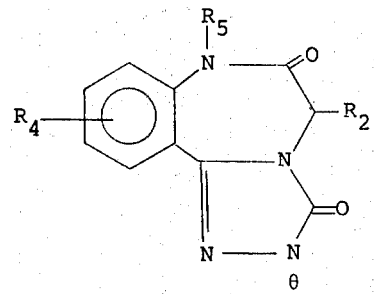

The salt of formula III is reacted with a compound having the formula $R_3$—X, wherein X can be chlorine, bromine, iodine, alkylsulfonate (e.g., methanesulfonate) or arylsulfonate (e.g., toluenesulfonate), to obtain a compound having the structure IV 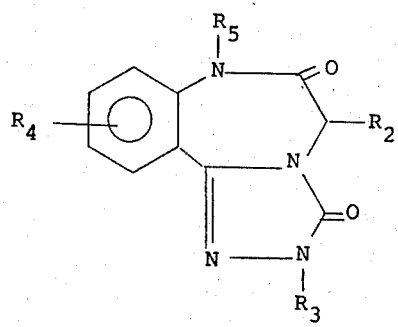

The reaction of a triazolobenzodiazepine of formula II with thallous ethoxide (or other base) can be run in a nonreactive polar solvent, e.g. dimethylformamide, at a temperature from about 0°C to 180°C, preferably at room temperature to 80°C for a period of about 1 minute to 5 hours, preferably from 10 minutes to 1 hour. The reaction of a salt of formula III with a compound of the structure $R_3$—X can be run at about 50°C to 200°C for a period of about 30 minutes to 72 hours, preferably at 80°C to 140°C for 2 to 24 hours. When $R_3$ is phenyl, a copper catalyst is used.

Reduction of a triazolobenzodiazepine of formula IV wherein $R_5$ is benzyl yields the corresponding compound having the structure

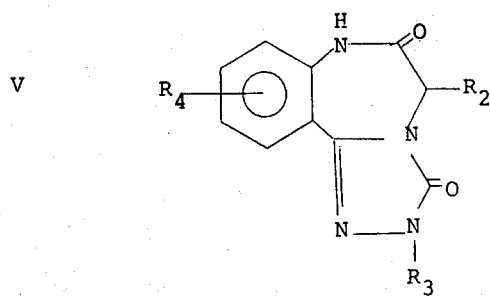

V

The reduction can be accomplished using hydrogen under pressure in the presence of a catalyst, e.g. palladium, or Raney nickel, or by reacting the compound with anhydrous liquid hydrofluoric acid.

The preparation of the compounds of formula II is set forth in co-pending U.S. patent application Ser. No. 447,719, filed Mar. 4, 1974 now U.S. Pat. No. 3,895,005 issued July 15, 1975.

The compounds of formula II are prepared using as starting materials compounds having the formula

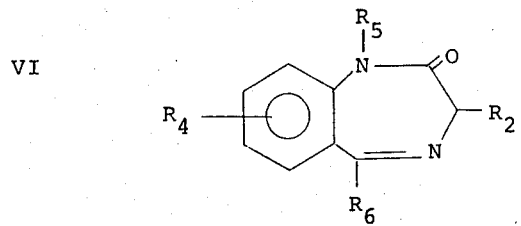

VI wherein $R_6$ can be halogen (preferably bromine or chlorine), sulfhydryl, alkoxy, alkylthio, or phenylalkylthio. The compounds of formula VI are known; see for example, U.S. Pat. No. 3,414,563 and Swiss Patent 485,742.

Reaction of a benzodiazepine of formula VI with an alkyl carbazate having the formula

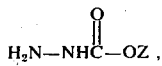

wherein Z is alkyl, yields a compound having the structure

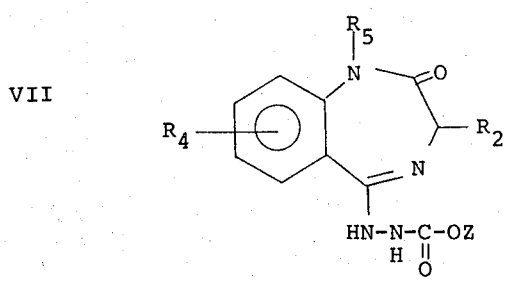

VII

The reaction can be run without a solvent, or in a nonreacting organic solvent, at a temperature of from about 50°C to 250°C for about 5 minutes to 24 hours, preferably from about 80°C to 140°C for about 30 minutes to 6 hours. The benzodiazepine of formula VI, and the alkyl carbazate are reacted in approximately a 1:1 molar ratio. Heating a compound of formula VII at an elevated temperature, e.g. 80°C to 200°C, preferably 100°C to 180°C, yields the corresponding compound of formula II.

The compounds of formula I wherein $R_1$ is alkyl are preferred and those wherein $R_1$ is methyl are most preferred.

The compounds of formula I wherein $R_2$ is hydrogen are preferred.

The following examples are specific embodiments of this invention.

EXAMPLE 1

10-Chloro-2,7-dihydro-2,7-dimethyl-3H-s-triazolo[4,3-d] [1,4]benzodiazepine-3,6(5H)-dione 10-Chloro-2,7-dihydro-7-methyl-3H-s-triazolo[4,3-d]-[1,4]benzodiazepene-3,6 (5H)-dione (6.0 g) is dissolved in 90 ml of dimethylformamide at 45°C and 5.37 g of thallous ethoxide is added. The solution is stirred at room temperature for 2 hours, during which time a precipitate forms. The addition of 3 volumes of ether completely precipitates the salt. The solid is filtered and dried in vacuo at room temperature to yield 9.5 g of the thallium salt.

The salt is suspended in 100 ml of methyliodide and refluxed for 18 hours. The reaction mixture is filtered and the solid is dried in vacuo to yield 3.7 g of material. The solid is dissolved in chloroform and chromatographed on a dry column of 75 g of silica gel. The column is eluted with 600 ml of chloroform/ethyl acetate (3:2) to yield 1.3 g of material which is recrystallized from chloroform/methanol (1:1) to yield 1.0 g of the title compound, melting point 292°–294°C.

EXAMPLE 2

10-Chloro-2,7-dihydro-7-methyl-2-phenyl-3H-s-triazolo[4,3-d] [1,4]benzodiazepine-3,6 (5H)-dione 10-Chloro-2,7-dihydro-7-methyl-3H-s-triazolo[4,3-d]-[1,4]benzodiazepine-3,6 (5H)-dione (1.0 g), 0.95 g of copper powder and 665 mg of potassium acetate are refluxed with 18 ml of bromobenzene for 6 hours. After cooling the reaction mixture is diluted with 20 ml of methylene chloride and filtered through a Celite pad. The insoluble salt and Celite are washed with an additional 25 ml of methylene chloride. The filtrates are combined, washed with 40 ml of 1N ammonium hydroxide and the alkaline layer is extracted with 25 ml of methylene chloride. The organic layers are combined, dried over anhydrous sodium sulfate, filtered and the solvent removed under vacuum. The residue is heated with 250 ml of chloroform, filtered and the solvent removed from the filtrate under vacuum. The product obtained is combined and stirred with 200 ml of methylene chloride for 2 days. The Celite pad is also stirred for 2 days with 200 ml of methylene chloride. Both mixtures are filtered, combined and the solvent removed under vacuum to yield 600 mg of material. The material is chromatographed on silica gel plates and the major band extracted with methylene chloride/ethyl acetate (1:1) to yield 150 mg of material. Recrystallation from methanol and water yields 94 mg of the title compound, melting point 174°–175°C.

EXAMPLES 3 and 4

Following the procedure of Example 2, but substituting the compound listed in column I for 10-chloro-2,7-dihydro-7-methyl-3H-s-triazolo[4,3-d][1,4]benzodiazepine-3,6(5H)-dione, the compound listed in column II is obtained.

| Example | Column I | Column II |
|---------|----------|-----------|
| 3 | 7-ethyl-2,7-dihydro-3H-s-triazolo[4,3-d][1,4]benzodiazepine-3,6(5H)-dione | 7-ethyl-2,7-dihydro-2-phenyl-3H-s-triazolo-[4,3-d][1,4]benzodiazepine-3,6(5H)-dione |
| 4 | 2,7-dihydro-10-(methoxy)-7-methyl-3H-s-triazolo[4,3-d][1,4]benzodiazepine-3,6(5H)-dione | 2,7-dihydro-10-(methoxy)-7-methyl-2-phenyl-3H-s-triazolo[4,3-d][1,4]benzodiazepine-3,6(5H)-dione |

EXAMPLE 5

10-Chloro-2,7-dihydro-7-methyl-2-(phenylmethyl)-3H-s-triazolo[4,3-d][1,4]benzodiazepine-3,6 (5H)-dione stripped off and the residue recrystallized from isopropanol to give 0.2 g of the title compound, melting point 120°–122° C.

EXAMPLES 6 – 14

Following the procedure of Example 5, but substituting the compound listed in column I for 10-chloro-2,7-dihydro-7-methyl-3H-s-triazolo[4,3-d][1,4]benzodiazepine-3,6 (5H)-dione and the compound listed in column II for benzyl bromide, the compound listed in column III is obtained.

| Example | Column I | Column II | Column III |
|---------|----------|-----------|------------|
| 6 | 7-benzyl-2,7-dihydro-10-(trifluoromethyl)-3H-s-triazolo[4,3-d][1,4]benzodiazepine-3,6(5H)-dione | 4-bromo-1-phenylbutane | 7-benzyl-2,7-dihydro-2-(4-phenylbutyl)-10-(trifluoromethyl)-3H-s-triazolo[4,3-d][1,4]benzodiazepine-3,6(5H)-dione |
| 7 | 2,7-dihydro-7-methyl-10-nitro-3H-s-triazolo[4,3-d][1,4]benzodiazepine-3,6(5H)-dione | 3-bromo-1-(2-chlorophenyl)butane | 2,7-dihydro-7-methyl-10-nitro-2-[3-(2-chlorophenyl)-1-methylpropyl]-3H-s-triazolo[4,3-d][1,4]benzodiazepine-3,6(5H)-dione |
| 8 | 10-ethylthio-2,7-dihydro-7-methyl-3H-s-triazolo[4,3-d][1,4]benzodiazepine-3,6(5H)-dione | 2-bromo-1-phenylbutane | 10-ethylthio-2,7-dihydro-7-methyl-2-[1-(phenylmethyl)propyl]-3H-s-triazolo[4,3-d][1,4]benzodiazepine-3,6(5H)-dione |
| 9 | 2,7-dihydro-7,10-dimethyl-3H-s-triazolo[4,3-d][1,4]benzodiazepine-3,6(5H)-dione | 2-bromo-1-(3,4-dichlorophenyl)ethane | 2,7-dihydro-7,10-dimethyl-2-[2-(3,4-dichlorophenyl)ethyl]-3H-s-triazolo[4,3-d][1,4]benzodiazepine-3,6(5H)-dione |
| 10 | 2,7-dihydro-5,7-dimethyl-10-(trifluoromethyl)-3H-s-triazolo[4,3-d][1,4]benzodiazepine-3,6(5H)-dione | 3-bromo-1-(2-methoxyphenyl)propane | 2,7-dihydro-5,7-dimethyl-2-[3-(2-methoxyphenyl)propyl]-10-(trifluoromethyl)-3H-s-triazolo[4,3-d][1,4]benzodiazepine-3,6-(5H)-dione |
| 11 | 9-bromo-2,7-dihydro-7-phenyl-3H-s-triazolo[4,3-d][1,4]benzodiazepine-3,6(5H)-dione | 2-bromo-1-(3,5-dimethylphenyl)ethane | 9-bromo-2,7-dihydro-2-[2-(3,5-dimethylphenyl)ethyl]-7-phenyl-3H-s-triazolo[4,3-d][1,4]benzodiazepine-3,6(5H)-dione |
| 12 | 7-benzyl-10-cyano-2,7-dihydro-3H-s-triazolo[4,3-d][1,4]benzodiazepine-3,6(5H)-dione | 4-fluorophenylmethyl bromide | 7-benzyl-10-cyano-2,7-dihydro-2-(4-fluorophenylmethyl)-3H-s-triazolo[4,3-d][1,4]benzodiazepine-3,6(5H)-dione |
| 13 | 7-benzyl-10-chloro-2,7-dihydro-3H-s-triazolo[4,3-d][1,4]benzodiazepine-3,6(5H)-dione | 1-bromo-2-methylpropane | 7-benzyl-10-chloro-2,7-dihydro-2-(2-methylpropyl)-3H-s-triazolo[4,3-d][1,4]benzodiazepine-3,6(5H)-dione |
| 14 | 10-ethyl-2,7-dihydro-7-phenyl-3H-s-triazolo[4,3-d][1,4]benzodiazepine-3,6(5H)-dione | 2-bromopropane | 10-ethyl-2,7-dihydro-2-(1-methylethyl)-7-phenyl-3H-s-triazolo[4,3-d][1,4]benzodiazepine-3,6(5H)-dione |

(5H)-dione

10-Chloro-2,7-dihydro-7-methyl-3H-s-triazolo[4,3-d]-[1,4]benzodiazepine-3,6 (5H)-dione (2.0 g) is dissolved in 30 ml of warm (ca 70°C) dimethylformamide and treated with 1.9 g of thallous ethoxide. After stirring at 60°C for 15 minutes the solution is diluted with 60 ml of ether and the resulting precipitate filtered off. The precipitate is dried at 25°C for 2 hours and then suspended in 100 ml of refluxing toluene and treated with 2.6 g of benzyl bromide. Refluxing is continued for 18 hours. The hot reaction mixture is filtered throughout infusorial earth and the filtrate is stripped of solvent. The residue is taken up in chloroform and washed through a 5 × 10 cm. column of neutral alumina with 1 liter of chloroform:ethyl acetate (6:4). The solvents are

EXAMPLE 15

10-Chloro-2,7-dihydro-2-(2-methylpropyl)-3H-s-triazolo[4,3-d][1,4]benzodiazepine-3,6 (5H)-dione 7-Benzyl-10-chloro-2,7-dihydro-2-(2-methylpropyl)-3H-s-triazolo[4,3-d][1,4]benzodiazepine-3,6 (5H)-dione (0.01 mole, prepared by the procedure of Example 13) is hydrogenated at 60°C in 300 ml of acetic acid containing 0.3 g of pre-reduced Raney nickel. The initial hydrogen pressure is 60 p.s.i. The reduction is stopped after 0.01 mole of hydrogen is absorbed, the catalyst is filtered off, and the solvent is evaporated. The residue is stirred with water and the title compound is filtered off and dried.

What is claimed is:

1. A compound having the structure

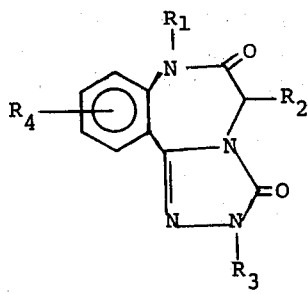

wherein $R_1$ is hydrogen, alkyl, phenyl or benzyl; $R_2$ is hydrogen or alkyl $R_3$ is alkyl, phenyl or arylalkyl; and $R_4$ is hydrogen, halogen, nitro, cyano, trifluoromethyl, alkyl, alkoxy or alkylthio; and wherein alkyl in all instances is alkyl of 1 to 4 carbon atoms, alkoxy in all instances is alkoxy of 1 to 4 carbon atoms and aryl in all instances is phenyl or phenyl substituted with 1 or 2 alkyl, alkoxy or halogen substituents.

2. A compound in accordance with claim 1 wherein $R_1$ is hydrogen.

3. A compound in accordance with claim 1 wherein $R_1$ is alkyl.

4. A compound in accordance with claim 1 wherein $R_1$ is phenyl.

5. A compound in accordance with claim 1 wherein $R_1$ is benzyl.

6. A compound in accordance with claim 1 wherein $R_2$ is hydrogen.

7. A compound in accordance with claim 1 wherein $R_2$ is alkyl.

8. A compound in accordance with claim 1 wherein $R_3$ is alkyl.

9. A compound in accordance with claim 1 wherein $R_3$ is phenyl.

10. A compound in accordance with claim 1 wherein $R_3$ is arylalkyl.

11. A compound in accordance with claim 1 wherein $R_4$ is hydrogen.

12. A compound in accordance with claim 1 wherein $R_4$ is halogen.

13. A compound in accordance with claim 12 wherein $R_4$ is chlorine.

14. The compound in accordance with claim 1 having the name 10-chloro-2,7-dihydro-2,7-dimethyl-3H-s-triazolo-[4,3-d] [1,4]benzodiazepine-3,6 (5H)-dione.

15. The compound in accordance with claim 1 having the name 10-chloro-2,7-dihydro-7-methyl-2-phenyl-3H-s-triazolo[4,3-d] [1,4]benzodiazepine-3,6 (5H)-dione.

16. The compound in accordance with claim 1 having the name 10-chloro-2,7-dihydro-7-methyl-2-(phenylmethyl)-3H-s-triazolo[4,3-d] [1,4]benzodiazepine-3,6 (5H)-dione.

* * * * *